United States Patent [19]

Taoda et al.

[11] Patent Number: 5,556,411
[45] Date of Patent: Sep. 17, 1996

[54] TROCAR ASSEMBLY HAVING A CANNULA RETAINING MEMBER

[75] Inventors: Toshimitsu Taoda, Sennan-gun; Masao Horie, Ohtsu, both of Japan

[73] Assignees: Nissho Corporation, Osaka-fu; Getz Bros. Co., Ltd., Tokyo-to, both of Japan

[21] Appl. No.: 271,986

[22] Filed: Jul. 8, 1994

[30] Foreign Application Priority Data

Jul. 9, 1993 [JP] Japan .................................. 5-194076

[51] Int. Cl.$^6$ .................................. A61B 17/34
[52] U.S. Cl. .................................. 606/185; 604/164
[58] Field of Search .................................. 606/185, 167, 606/184; 604/264, 164–165, 134, 158, 194, 272, 198

[56] References Cited

U.S. PATENT DOCUMENTS

| | | | |
|---|---|---|---|
| 4,702,260 | 10/1987 | Wang | 604/264 X |
| 5,226,426 | 7/1993 | Yoon | 604/165 X |
| 5,242,427 | 9/1993 | Bilweis | 604/264 |
| 5,330,497 | 7/1994 | Freitas et al. | 606/185 |

FOREIGN PATENT DOCUMENTS

| | | |
|---|---|---|
| 0312219 | 9/1988 | European Pat. Off. . |
| 0350291 | 5/1989 | European Pat. Off. . |
| 0513962 | 1/1992 | European Pat. Off. . |
| 0546766 | 3/1992 | European Pat. Off. . |
| 0589452 | 9/1993 | European Pat. Off. . |
| 2024089 | 9/1969 | France . |
| 2311557 | 5/1976 | France . |
| 9304717 | 3/1993 | WIPO . |

*Primary Examiner*—Gary Jackson
*Assistant Examiner*—Nancy Mulcare

[57] ABSTRACT

A trocar assembly includes a cannula, a trocar needle fitted in a lumen of the cannula, a cannula-retaining member having a through-hole for inserting the cannula therein and being provided at a bottom thereof with an adhesive layer for fixing the cannula in place on the skin of a patient. The cannula is adapted to be held in the retaining member by engaging elements between them to permit the cannula to move forward continuously or continually through the through-hole of the retaining member as well as to fix the cannula in a desired position.

8 Claims, 4 Drawing Sheets

TROCAR ASSEMBLY HAVING A CANNULA RETAINING MEMBER

BACKGROUND OF THE INVENTION

1. Field of the Invention

The present invention relates to a trocar assembly and, more particularly, to a trocar assembly suitable for use in laparoscopic intra-corporeal operations.

2. Description of the Prior Art

In recent intra-corporeal surgeries, laparoscopic or endoscopic surgeries have been performed to avoid cutting the skin over wide ranges. Such laparoscopic surgeries are generally performed by piercing a Veress needle into the abdominal cavity of a patient in place, insufflating an insufflation gas (generally, carbon dioxide) into the abdominal cavity, removing the Veress needle from the abdominal cavity after the abdominal cavity has been insufflated sufficiently, introducing a trocar fitted with a rigid sheath with a diameter of 5 to 12 mm into the abdominal cavity through the same site of the puncture, and then introducing a laparoscope into the abdominal cavity through the sheath to perform an intra-corporeal operation. In such intra-corporeal operations, however, there is a fear that any internal organ in the abdominal cavity may be injured by a piercing edge of the trocar during insertion into the abdominal cavity.

To solve such a problem, it has been proposed to provide a protective sleeve on the trocar so as to cover a piercing edge of the trocar or to receive the trocar when the piercing edge of the trocar has passed through the peritoneum. Such a trocar fitted with the protective sleeve is adapted to penetrate the abdominal wall or peritoneum by pushing it in its longitudinal direction, and the protective sleeve serving as a safety mechanism of the trocar is so designed as to perform its function to cover the piercing edge of the trocar just when the piercing edge of the trocar is completely introduced into the abdominal cavity.

During insertion, the trocar is advanced by the external force applied thereto in the direction facing to the internal organs, notwithstanding the piercing edge of the trocar which has been protruded from the protective sleeve. Thus, it is difficult to prevent the internal organ completely from being injured by the piercing edge of the trocar even though the abdominal wall (peritoneum) has been spaced from the internal organs by insufflation.

SUMMARY OF THE INVENTION

It is therefore an object of the present invention to provide a trocar assembly for use in laparoscopic intra-corporeal operations, which is free from a fear of injures to internal organs and is capable of being introduced into the abdominal cavity safely.

According to the present invention there is provided a trocar assembly comprising a cannula or sleeve, a trocar fitted in a lumen of the cannula, and a cannula-retaining member having a through-hole for inserting the cannula therein and being provided at a bottom thereof with an adhesive layer for fixing the cannula in place on the skin of a patient, said cannula and the retaining member each having means for engagement with one another, said engaging means permitting the cannula to move forward continuously or continually through said through-hole of the retaining member as well as to fix the cannula in a desired position.

In a preferred embodiment, the engaging means is composed of an external thread winding around the outside of the cannula, and an internal thread winding around the through-hole of the cannula-retaining member.

In another preferred embodiment, the trocar assembly further includes a sheath for rotatably holding the trocar, the sheath is fitted in the cannula so as to be rotated or moved along with the cannula.

In still another preferred embodiment, the cannula is fitted with a trocar-retaining member at its proximal end to permit forward movement of the trocar along with the cannula.

In another embodiment, the interengaging means is composed of annular ribs formed around the outside of the cannula and spaced from one another at certain intervals, and one or more projections extending from the inside of the through-hole of the cannula-retaining member toward the axis thereof, said one or more projections being located on an imaginary circle and circumferencially spaced from one another, said annular ribs each having one or more cuts corresponding to the number of the projections of the cannula-retaining member, said cuts being so located that one cut of the rib being not aligned with the cut of the neighboring two ribs so as to permit continual movement of the cannula every when the cuts of the annular rib are aligned with the projections of the cannula-retaining member.

The head portion of the trocar of the present invention has a diameter larger than that of the lumen of a hollow member into which the needle is inserted.

In use, the cannula-retaining member is first adhered to the abdominal skin of a patient. Then, the trocar fitted with the cannula is inserted into the through-hole of the cannula-retaining member and then moved little by little towards the abdominal cavity continuously or continually by turning or turning and pressing it into the through-hole of the cannula-retaining member. Thus, the trocar is introduced into the abdominal cavity without causing injuries to the internal organs. If the trocar assembly has the engaging means composed of an external thread winding around the outside of the cannula and an internal thread winding around the inside or through-hole of the cannula-retaining member, the trocar is moved forward little by little by turning the cannula at a slow rate, thus making it possible to minimize danger to the internal organs. Further, the cannula is held by the cannula-retaining member at a position where the cannula is prevented from rotating or at a position where the cannula is stopped after the cannula is turned slightly so that the cuts in the rib are out of alignment with the projections of the retaining member, thus making it possible to prevent the cannula from dislodging from the skin.

These and other objects and features of the present invention will become clear from the following description taken in conjunction with preferred embodiments thereof with reference to the accompanying drawings throughout in which like parts are designated by like reference numerals. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
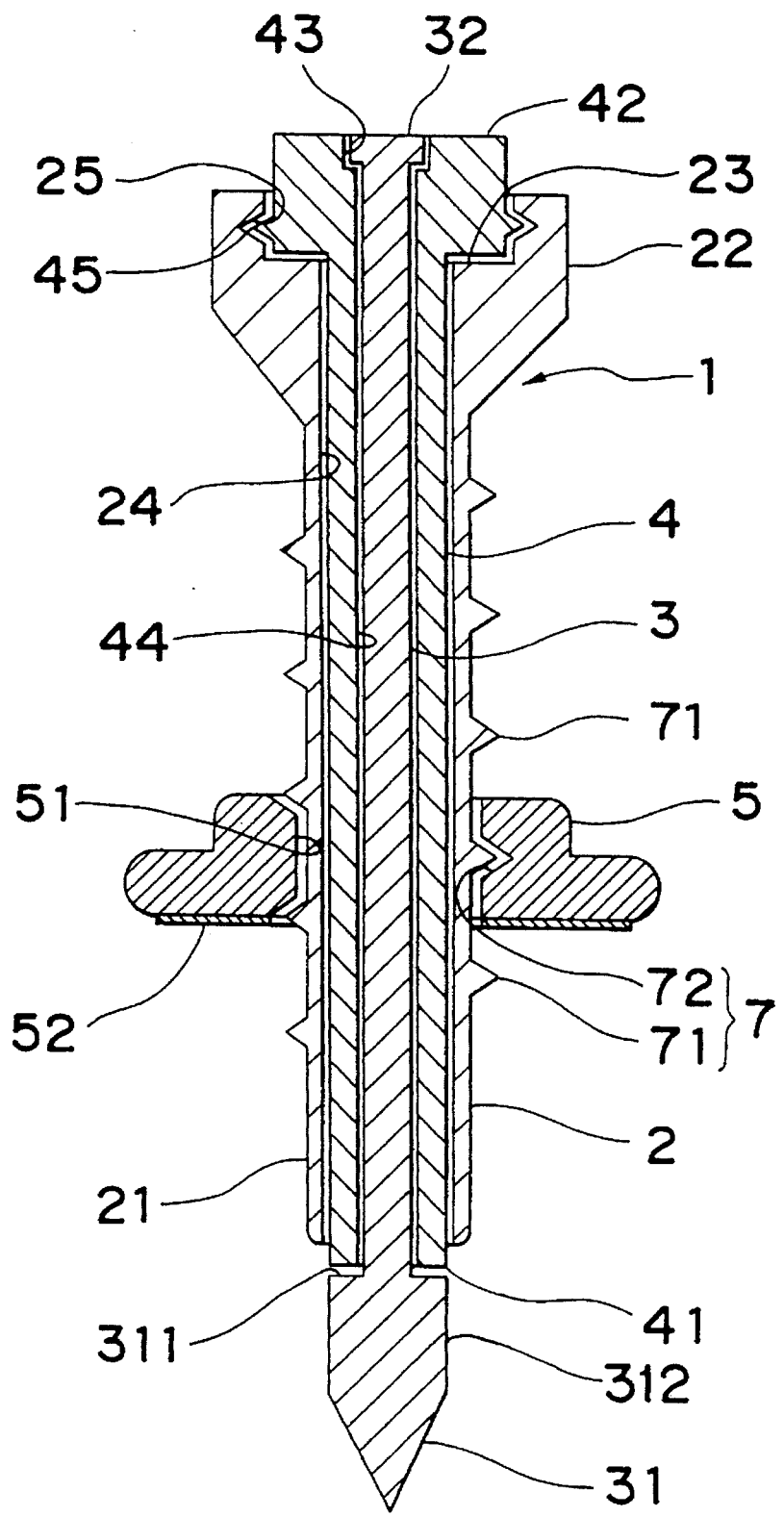
FIG. 1 is a cross section illustrating one embodiment of a trocar assembly according to the present invention.

Referring to FIG. 1, there is shown a trocar assembly 1 of the present invention comprising a cannula 2, a trocar needle 3 fitted with a sheath 4 positioned in a lumen 24 of the cannula 2, and a cannula-retaining member 5 having a through-hole 51 and an adhesive layer 52 provided at a bottom thereof. The trocar assembly 1 further includes engaging means 7 formed between the cannula-retaining member 5 and the cannula 2 to permit the cannula 2 to move forward little by little continuously through the through-hole 51 of the cannula-retaining member 5 as well as to fix the cannula 2 in a desired position.

The cannula 2 is composed of a small tubular member with a lumen 24 having an outer diameter of 5 to 12 mm for the general purpose, used for insertion of a surgical instrument such as a laparoscope into the abdominal cavity through the lumen 24 after the trocar needle 3 has been removed therefrom. The cannula 2 is provided with an external thread 71 except for a distal end 21 and a proximal end 22 thereof, to form the interengaging means 7 in cooperation with an internal thread 72 formed in the through-hole 51 of the cannula-retaining member 5 mentioned below.

At one end, i.e., the distal end 21 of the cannula 2, the outer corner is tapered or rounded off so as to lower the insertion force of the cannula 2 into the abdominal cavity. The other end, i.e., the proximal end 22 of the cannula 2 is increased in outer diameter to facilitate the rotation of the cannula 2 as the cannula 2 is engaged with the cannula-retaining member 5 by the interengaging means 7. The cannula 2 is provided in its proximal end 22 with a cylindrical recess 23 for receiving a proximal end 42 of the sheath 4 mentioned below. The recess 23 has a common axis with the lumen 24 of the cannula 2 and communicates with the lumen 24 thereof. The cannula 2 is further provided in its recess 23 with an internal thread 25 adapted to be engaged with an external thread 45 of the sheath 4 so that the screw-engagement between the cannula 2 and the sheath 4 is tightened when the cannula 2 is turned clockwise.

The trocar needle 3 is an elongated piercing member with a diameter slightly smaller than that of a lumen 44 of the sheath 4, having a sharp-edged portion 31 at the distal end and a disk-like head 32 at the proximal end. The head 32 is generally designed so as to have a diameter larger than that of the lumen 44 of the sheath 4 into which the trocar needle 3 is movably inserted, but smaller than that of the recess 43 of the proximal end 42 of the sheath 4. The sharp-edged portion 31 of the trocar needle 3 has a base 312 with a diameter slightly smaller than that of the lumen 24 of the cannula 2 and approximately equal to the outer diameter of the sheath 4. The trocar needle 3 is positioned in the lumen 44 of the sheath 4 for piercing the abdominal cavity in place.

The sheath 4 is a tubular member having a distal end 41 and a large-sized proximal end 42, made for rotatably holding the trocar needle 3. The sheath 4 is located in the lumen 24 of the cannula 2 so as to be rotated and moved forward together with the cannula 2 in a body without causing rotation of the trocar needle 3 even if the sheath 4 is rotated. For that purposes, the sheath 4 is so designed as to have an outside diameter slightly smaller than the diameter of the lumen 24 of the cannula 2 and an inside diameter slightly larger than the diameter of the trocar needle 3. Further, the proximal end portion 42 of the sheath 4 has a configuration corresponding to the shape of the recess 23 of the cannula 2 and is provided with an annular recess 43 having a common axis with the lumen 44 of the sheath 4 for receipt of the proximal end 32 of the trocar needle 3.

The distal end 41 of the sheath 4 extends to or beyond the distal end of the cannula 2 and terminates at the proximal end portion of the trocar needle 3 so as to come into contact with the proximal end surface 311 of the sharp-edged portion 31 of the trocar needle 3 when the sheath 4 is pushed forward. It is preferred to provide a clearance between the proximal end surface 311 of the sharp-edged portion 31 of the trocar needle 3 and the distal end 41 of the sheath 4 so that the operator can feel that the trocar needle 3 has broken through the fascia or the abdominal wall.

The cannula-retaining member 5 is a disk-shaped member having a through-hole 51 used for retaining the cannula 2 in place. The cannula-retaining member 5 is provided with an adhesive layer 52 at its bottom for adhesion to the skin of the patient to be operated on. As an adhesive material for the adhesive layer, there may be used those such as rubber adhesive, acrylic adhesive, silicone adhesive and the like. Among them, it is preferred to use pressure-sensitive adhesives such as poly(acryl ester), poly(vinyl ether) and the like. If necessary, the adhesive may contain a germicide such as iodine incorporated therein to prevent infection.

The through-hole 51 is threaded to form an internal thread 72 for engagement with the external thread 71 of the cannula 2. Thus, the internal thread 72 constitutes the interengaging means 7 together with the external thread 71 of the cannula 2.

Figure 2:
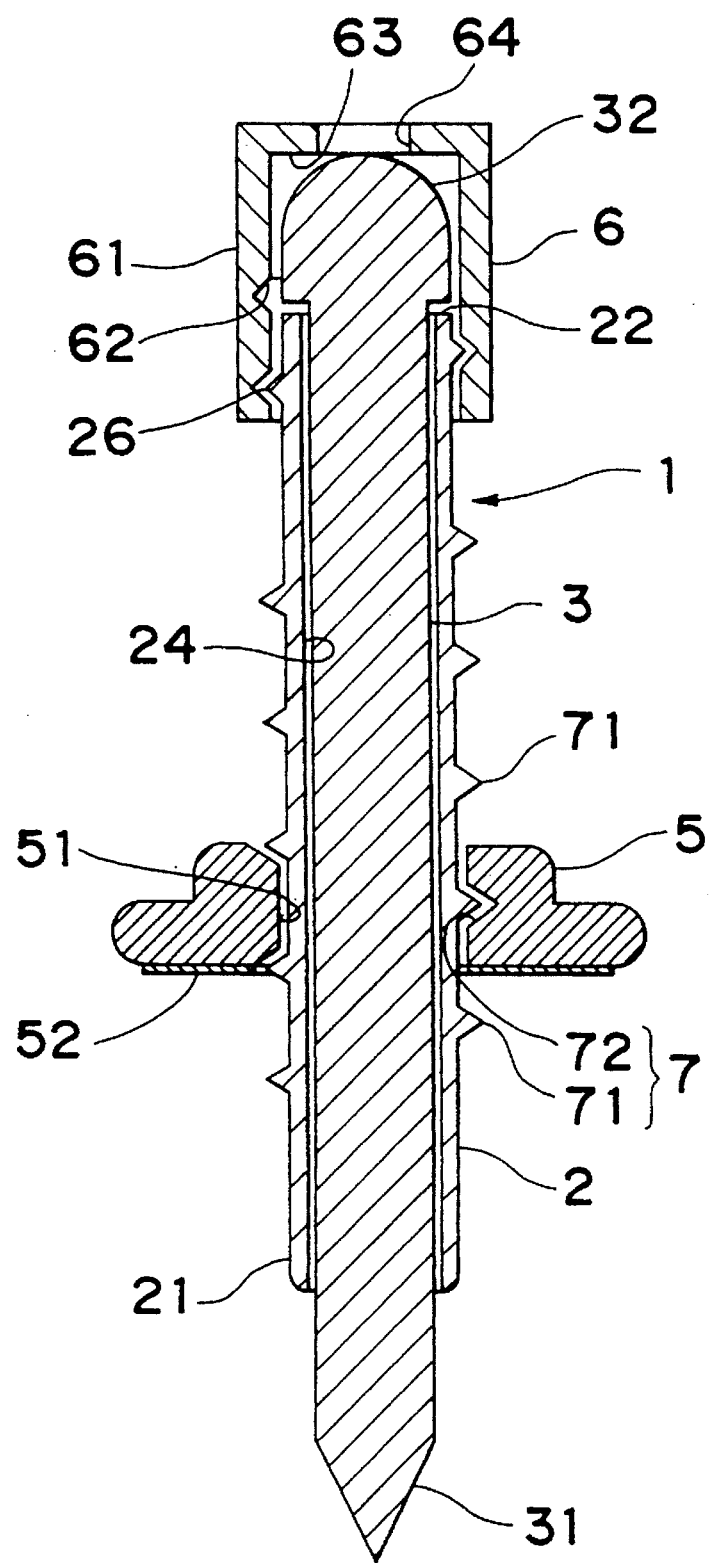
FIG. 2 is a cross section illustrating another embodiment of the present invention.

Referring now to FIG. 2, there is shown another embodiment of a trocar assembly 1 comprising a cannula 2, a trocar needle 3 positioned in a lumen 24 of the cannula 2, and a cannula-retaining member 5 having a through-hole 51 and an adhesive layer 52 provided at a bottom thereof. The cannula-retaining member 5 has the same construction as that of the embodiment shown in FIG. 1.

The cannula 2 is a slender, small straight tubular member with an external thread 26 and 71 winding around the outside except for its distal end. Further, the cannula 2 is removably provided with a trocar needle holding member 6 at its proximal end. The trocar-holding member 6 is a cap-like member having an internal thread 62 at its skirt 61 and a through-hole 64 at a top 63 thereof and is screw-mounted on the proximal end of the cannula 2 to prevent rotation of the trocar needle 3 during forward movement of the cannula 2.

The trocar needle 3 is a sharp-pointed solid member having a rounded head 32 at its proximal end. The main part of the trocar needle 3 has a uniform diameter slightly smaller than that of the lumen 24 of the cannula 2, while the head 32 has a diameter larger than that of the lumen 24 of the cannula 2.

In the structure shown in FIG. 2, the head 32 of the trocar needle 3 is positioned between the top 63 of the trocar needle holding member 6 and the proximal end 22 of the cannula 2 and brought into contact with the top 63 of the trocar needle holding member 6 when introducing the cannula 2 into the abdominal cavity. Thus, the trocar needle 3 is prevented from longitudinal movement within the lumen 24 of the cannula 2. However, the trocar needle 3 is rotatable as the trocar 3 is disengaged from the cannula 2 and the trocar needle holding member 6. Thus, when the cannula 2 and the trocar needle holding member 6 are turned clockwise, the trocar needle 3 moves forward together with the cannula 2 without rotating. In this embodiment, it is preferred to provide the external thread 26 and internal screw 62 so that the thread engagement between them is not loosened when the cannula 2 and the trocar needle holding member 6 are turned clockwise, i.e, the thread engagement is tightened when the cannula 2 is turned counterclockwise with respect to the trocar needle member 6.

Figure 3:
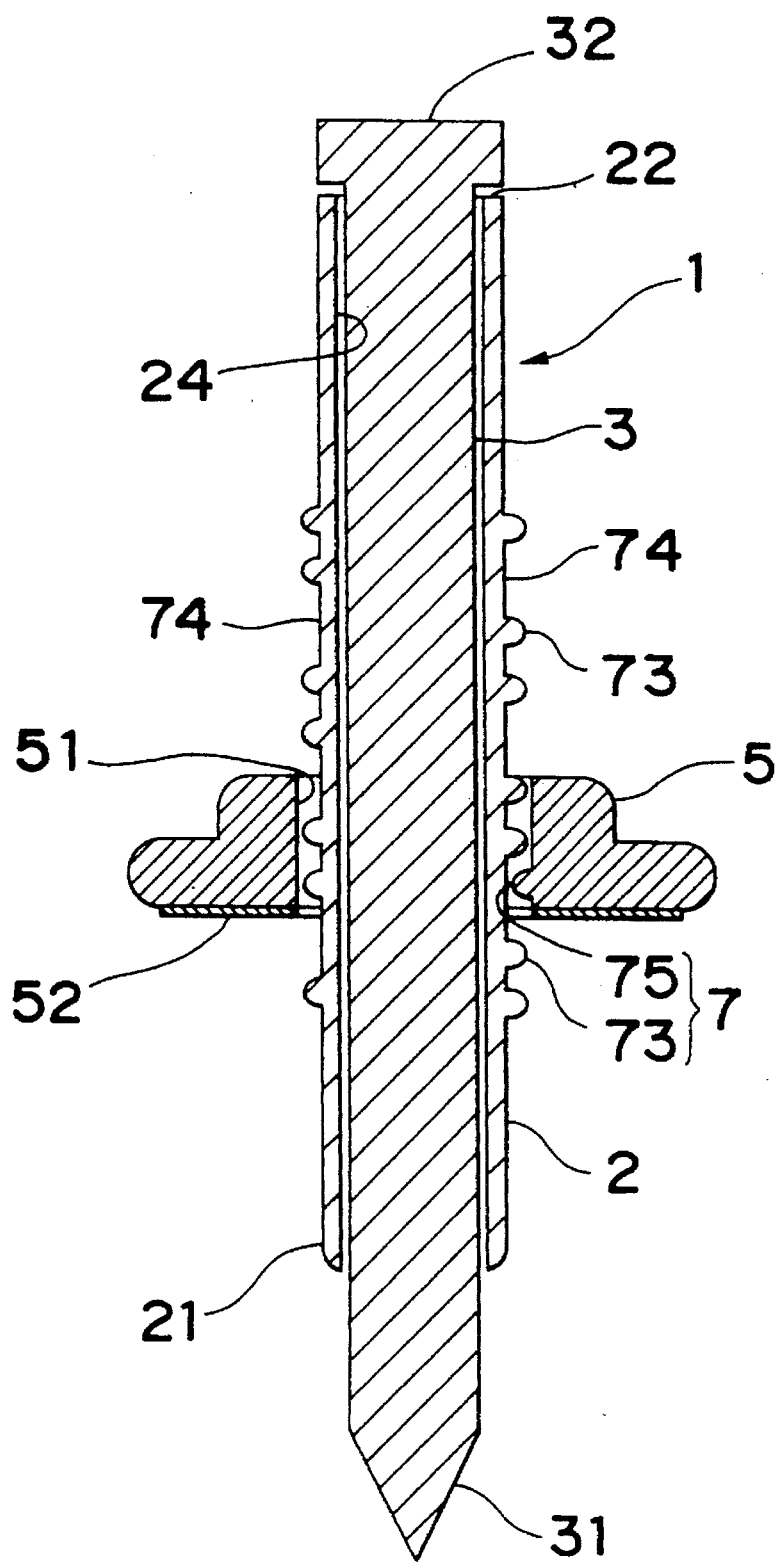
FIG. 3 is a cross section illustrating still another embodiment of the present invention.
Figure 4:
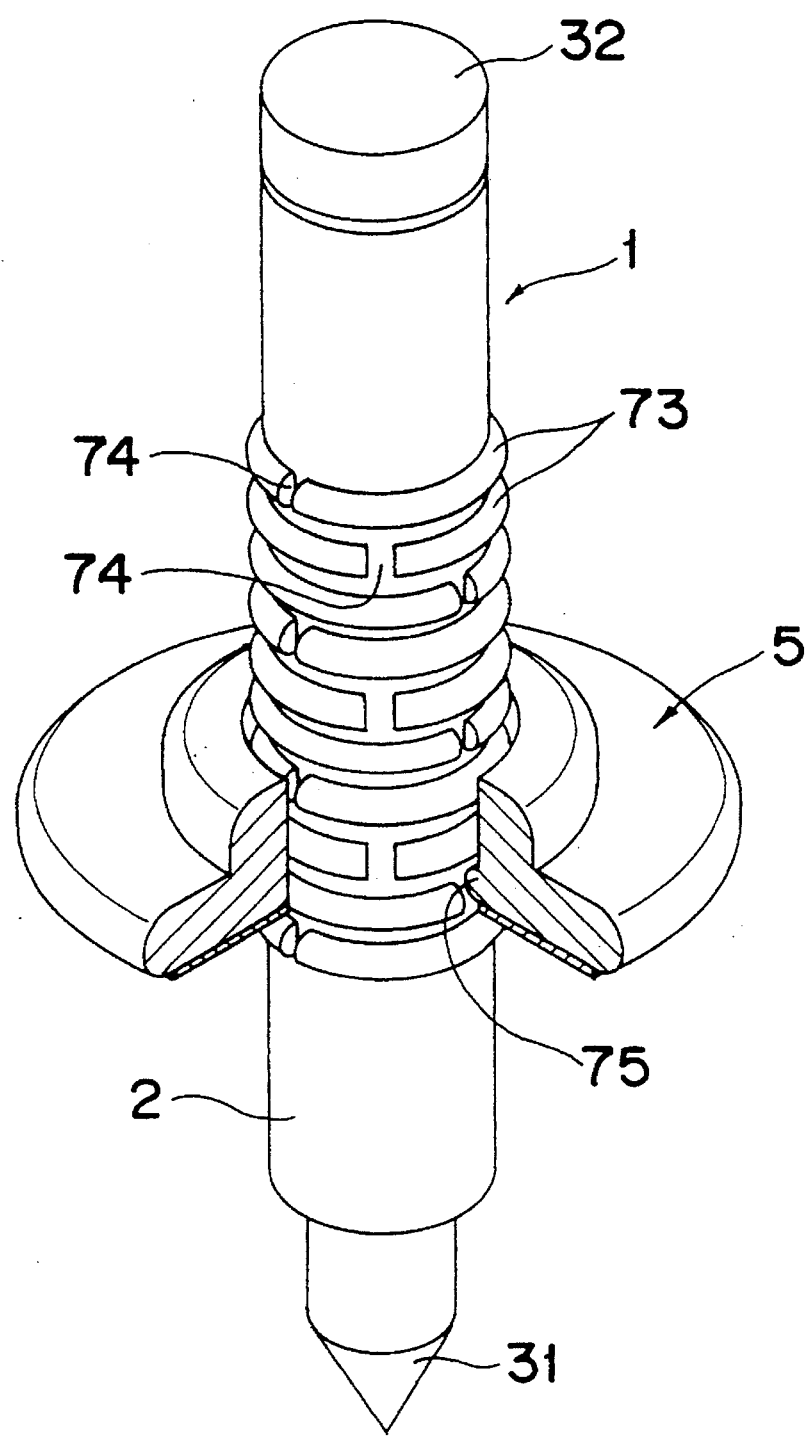
FIG. 4 is a partially cutaway perspective view of a trocar assembly of FIG. 3.

FIG. 3 shows another embodiment of a trocar assembly 1 comprising a cannula 2, a trocar needle 3 positioned in a lumen 24 of the cannula 2, and a cannula-retaining member 5 having a through-hole 51 and an adhesive layer 52 provided at a bottom thereof. The cannula 2 is a slender, small straight tubular member with a lumen 24 and is provided with a plurality of annular ribs 73 extending outwardly for engagement with the cannula-retaining member 5. The annular ribs 73 are arranged with certain spaces between them and respectively provided with one or more narrow cuts 74 at regular intervals such that each cut in one annular rib 73 is not aligned with the cut 74 in the neighboring one or two ribs 73.

The cannula-retaining member 5 is further provided on its inside with one or more projections 75 corresponding to the number of the cuts 74 in the annular rib 73 of the cannula 2. These projections 75 extend from the wall of the through-hole 51 thereof toward the axis thereof and are arranged on the imaginary circle at regular intervals.

In use, the cannula 2 fitted with the trocar needle 3 is inserted into the cannula-retaining member 5 until its lowermost annular rib 73 comes into contact with the projections 75 of the cannula-retaining member 5. The cannula 2 is turned so that the cuts 74 in the lowermost rib 73 are aligned with the projections 75 of the cannula-retaining member 5, and pushed downwardly to permit the cannula 2 to move forward until its rib 73 next to the lowermost rib 73 comes into contact with the projections 75 of the cannula-retaining member 5. By repeating the above turning and pushing operations, the cannula 2 is moved forward continually step by step.

The use of the trocar assembly 1 according to the present invention is explained below in detail, taking an application of the trocar assembly of FIG. 1 to the laparoscopic-cholecystectomy by way of example.

First, the skin of the abdomen of a patient is cut below or above the navel to form an incision with a length of 1 cm, through which a Veress needle is introduced into the pelvic cavity. After a correct position of the Veress needle has been confirmed, the Veress needle is connected to an automatic insufflator to insufflate carbon dioxide gas into the abdominal cavity. The insufflation is carried out by first introducing the carbon dioxide gas into the abdominal cavity at a low flow rate, then increasing the flow rate after no abnormal increase in intra-abdominal pressure is confirmed by palpation or percussion, and continuing the introduction of the carbon dioxide gas until the intra-abdominal pressure has become about 10 to 12 mmHg. After completion of the insufflation, the Veress needle is removed from the skin.

Then, the cannula-retaining member 5 of the present invention is fixed to the skin by adhesion so that the through-hole 51 thereof overlaps the incision from which the Veress needle has been removed. The cannula 2 fitted with the trocar needle 3 is inserted into the through-hole 51 of the cannula-retaining member 5 and then introduced into the abdominal cavity by turning the cannula 2 clockwise. After confirming that the cannula 2 has been passed through the peritoneum, the trocar needle 3 is removed from the cannula 2 together with the sheath 4 and then a laparoscope is introduced into the abdominal cavity through the cannula 2, thereby confirming that the internal organs are free from injuries.

The insufflation is performed again to keep the intra-abdominal pressure to 12 to 14 mmHg by connecting the automatic insufflator to the cannula 2.

Additional trocar assemblies may than be introduced into the abdominal cavity in place while observing the abdominal cavity with the laparoscope. If any adhesion is observed around the cholecyst, adhesiotomy is performed. After the cholecyst has been drawn with two pairs of forceps, a cystic duct is denuded with dissecting forceps, or a high frequency cautery or a laser, clipped with three clip appliances (two for the central parts and one for the cervical part of the cystic duct), and then cut at the central part thereof with a cutting forceps. The same treatments are applied to the cystic artery. During the treatment of the cystic duct and cystic artery, the cholangiography is performed to confirm the cystic duct and no injury of the bile duct when the presence or location of choledocholith, or the relationship between the cystic duct and the choledochus cannot be determined.

After completing the treatment of the cystic duct and the cystic artery, the cholecyst is detached from the cholecystic matrix, starting from the collum vesicae felleae toward the lower part. The collum vesicae felleae of the detached cholecyst is then grasped by vulsellum forceps to draw out the collum vesicae felleae of the cholecyst through the cannula 2 and then the bile is removed from the cholecyst to contract the cholecyst. The cholecyst is then taken out from the abdominal cavity after crushing gallstones and removing the resultant pieces, if necessary. Then, the cholecystic matrix and thereabout are sufficiently washed with a saline solution and the abdominal cavity is degassed after no bleeding, bilious exudation and abnormality are confirmed by the laparoscope. The cannula 2 is then removed from the abdominal wall for sutures of the incision wounds.

As will be understood from the above, the present invention provides the following advantages:

(1) It is possible to introduce the trocar assembly into the abdominal cavity of a patient without injuring the internal organs since the cannula fitted with the trocar needle can be moved forward little by little continuously or continually by inserting it into the through-hole of the cannula-retaining member adhered to the abdominal wall of the patient.

(2) In the trocar assembly including the engaging means composed of an external thread formed around the outside the cannula and an internal thread formed around the inside of the cannula-retaining member, there is no danger of injuring the internal organs since the cannula can be moved forward little by little continuously by turning it at a slow rate.

(3) It is possible to prevent the cannula from dislodging from the abdominal skin as the cannula is fixed to the cannula-retaining member at a position where the cannula is prevented from rotating or a position where the cannula is stopped after the cannula it turned slightly so that the cuts in the rib are out of alignment with the projections of the retaining member.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims.

What is claimed is:

1. A trocar assembly comprising a cannula, a sheath located in said cannula so as to be rotated and moved along therewith, a trocar needle rotatably held by the sheath, said trocar needle including a sharp-edged portion having a diameter larger than a diameter of said sheath, and a cannula-retaining member having a through-hole for inserting the cannula therein and being provided at a bottom thereof with an adhesive layer for fixing the cannula in place on the skin of a patient, said cannula and the cannula-retaining member each having means for engagement with one another, said engagement means permitting the cannula to move forward continuously or continually through said through-hole of the cannula-retaining member as well as to fix the cannula in a desired position.

2. The trocar assembly according to claim 1, wherein the engagement means is composed of an external thread winding around the outside of the cannula, and an internal thread winding around the through-hole of the cannula-retaining member.

3. The trocar assembly according to claim 1, wherein the cannula is fitted with a trocar needle holding member at its proximal end to permit forward movement of the trocar needle along with the cannula.

4. The trocar assembly according to claim 1, wherein the engagement means is composed of annular ribs formed around the outside of the cannula and spaced from one another at certain intervals, and one or more projections extending from the inside of the through-hole of the cannula-retaining member toward the axis thereof, said one or more projections being located on an imaginary circle and circumferencially spaced from one another, said annular ribs each having one or more cuts corresponding to the number of the projections of the cannula-retaining member, said cuts being so located that one cut of the rib is not aligned with the cut of the neighboring two ribs so as to permit continual movement of the cannula when the cuts of the annular rib are aligned with the projections of the cannula-retaining member.

5. A trocar assembly comprising a cannula, a trocar needle fitted in a lumen of the cannula, and a cannula-retaining member having a through-hole for inserting the cannula therein and being provided at a bottom thereof with an adhesive layer for fixing the cannula in place on the skin of a patient, wherein the cannula is fitted with a trocar needle holding member at its proximal end to permit forward movement of the trocar needle along with the cannula.

6. The trocar assembly according to claim 5 wherein said cannula and the cannula-retaining member each have means for engagement with one another, said engagement means permitting the cannula to move forward continuously or continually through said through-hole of the cannula retaining member as well as to fix the cannula in a desired position.

7. The trocar assembly according to claim 6, wherein the engagement means is composed of an external thread winding around the outside of the cannula, and an internal thread winding around the through-hole of the cannula-retaining member.

8. A trocar assembly comprising a cannula, a trocar needle fitted in a lumen of the cannula, and a cannula-retaining member having a through-hole for inserting the cannula therein and being provided at a bottom thereof with an adhesive layer for fixing the cannula in place on the skin of a patient, said cannula and the cannula-retaining member each having means for engagement with one another, said engagement means permitting the cannula to move forward continuously or continually through said through-hole of the cannula-retaining member as well as to fix the cannula in a desired position, wherein the engagement means is composed of annular ribs formed around the outside of the cannula and spaced from one another at certain intervals, and one or more projection extending from the inside of the through-hole of the cannula-retaining member toward the axis thereof, said one or more projections being located on an imaginary circle and circumferencially spaced from one another, said annular ribs each having one or more cuts corresponding to the number of the projections of the cannula-retaining member, said cuts being so located that one cut of the rib is not aligned with the cut of the neighboring two ribs so as to permit continual movement of the cannula when the cuts of the annular rib are aligned with the projections of the cannula-retaining member.

* * * * *